United States Patent [19]

Carmody

[11] Patent Number: 5,274,152
[45] Date of Patent: Dec. 28, 1993

[54] METHOD OF PREPARATION OF SODIUM ALUMINUM LACTATE

[75] Inventor: Walter J. Carmody, Orange County, N.Y.

[73] Assignee: Somerville Technology Group, Inc., Huguenot, N.Y.

[21] Appl. No.: 982,480

[22] Filed: Nov. 27, 1992

[51] Int. Cl.$^5$ .............................. C07F 5/06; A61K 7/38
[52] U.S. Cl. ........................................ 556/183; 424/68
[58] Field of Search .......................... 556/183; 424/68

[56] References Cited

U.S. PATENT DOCUMENTS

| | | | |
|---|---|---|---|
| 3,014,055 | 12/1961 | Johnson | 260/448 |
| 3,446,585 | 5/1969 | Tanabe | 23/143 |
| 3,542,919 | 11/1970 | Buth et al. | 424/68 |
| 4,560,783 | 12/1985 | Shioyama et al. | 556/183 |
| 4,601,340 | 7/1986 | Fodor et al. | 166/294 |

FOREIGN PATENT DOCUMENTS 0465269  5/1950  Canada .............................. 556/183

*Primary Examiner*—José G. Dees
*Assistant Examiner*—Porfirio Nazario
*Attorney, Agent, or Firm*—Kenneth P. Glynn

[57] ABSTRACT

The present invention is directed to a method of preparing sodium aluminum lactate by reacting aluminum lactate with sodium hydroxide is an aqueous medium. The reaction is carried out within the temperature range of about 20° C. to about 80° C. The weight ratio of aluminum lactate to sodium hydroxide is about 5.0:1 to about 8.0:1. The weight ratio of water to sodium hydroxide is about 0.8:1 to about 2.3:1.

10 Claims, No Drawings

METHOD OF PREPARATION OF SODIUM ALUMINUM LACTATE

BACKGROUND OF THE INVENTION

1. Field of the Invention

The present invention is directed to a method of making sodium aluminum lactate. More specifically, this invention involves preparation of sodium aluminum lactate by reaction of aluminum lactate with sodium hydroxide in an aqueous medium.

2. Prior Art Statement

Sodium aluminum lactate powder is well known as a non-irritating deodorant ingredient. Previously, manufacturing of this material had accomplished by reacting sodium aluminate, lactic acid and sodium hydroxide in batch process, however, this process was limited due to pH and viscosity instability of its liquid intermediate. The liquid intermediate has a pH drift and viscosity increase to the point of a semisolid gel after one to two days from the date of manufacture. The pH variation results in product quality variation, and an unstable viscosity means that only small quantities of liquids are prepared and used almost immediately.

SUMMARY OF THE INVENTION

The present invention is directed to a method of preparing sodium aluminum lactate by reacting aluminum lactate with sodium hydroxide is an aqueous medium. The reaction is carried out within the temperature range of about 20° C. to about 80° C. The weight ratio of aluminum lactate to sodium hydroxide is about 5:1 to about 8:1. The weight ratio of water to sodium hydroxide is about 8:1 to about 2.3:1.

DETAILED DESCRIPTION OF THE PRESENT INVENTION

A new method of preparation has been found that eliminates the pH and viscosity instability of liquid solutions of sodium aluminum lactate discussed above. This new method is useful in that a stable pH and viscosity allows commercial quantities of the liquid sodium aluminum lactate to be prepared and dried over several days. The stable pH of this new method means a constant liquid resulting in constant product quality.

The new method of preparation uses aluminum lactate, sodium hydroxide and water to prepare the pH and viscosity stable liquid intermediate. The use of aluminum lactate is new and useful. When aluminum is reacted with lactic acid, it forms a stable molecular species, aluminum lactate. The stability of the aluminum lactate prevents the formation of aluminum hydroxide when the sodium hydroxide is added to the solution. It is the formation of aluminum hydroxide that causes the pH shifts and viscosity increase. This method produces a liquid that has a constant pH and viscosity for greater than 45 days. When spray dried, a white free flowing powder is produced with an analysis such as the following:

| | |
|---|---|
| Percent Al | 7.9 |
| Percent Na | 14.1 |
| Percent lactic acid | 78.0 |

The reaction may be conducted in stepwise bulk fashion or on a continuous flow basis. The temperature range within which the process takes place is about 20° C. to about 80° C. Lower temperatures may work but would be too sluggish for commercial purposes. Higher temperatures shift the stoichiometry and are not cost effective from the standpoint of yield and from the standpoint of energy consumption.

In general, solid (powder) sodium hydroxide and aluminum lactate may be used. In preferred embodiments, the sodium hydroxide is first added to water and then the aluminum lactate is mixed into the sodium hydroxide solution. In other embodiments, aqueous sodium hydroxide (e.g. 50% aq.) is combined with additional water and then aluminum lactate is mixed in until dissolved. In any of the previous embodiments, aluminum lactate may be in aqueous solution and combined with the water and sodium hydroxide.

About 5.0:1 to about 8.0:1 of aluminum lactate to sodium hydroxide, based on weight, is used. Also, about 0.8:1 to about 2.3:1 of total water content to sodium hydroxide, based on weight is used.

The aluminum lactate may be formed by reacting aluminum with lactic acid. This process may, for example, be carried out as follows:

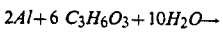

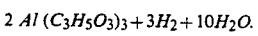

The constituents are reacted at room temperature and them maintained in aqueous form or dried and used in solid form and either is subsequently used in the present invention process. Alternatively, aluminum lactate product may be obtained from commercial suppliers.

The sodium aluminum lactate resulting from the present invention method is an aqueous product with stability and relatively constant, reliable viscosity. Thus, the present invention method consistently yields a product with a pH of about 3.0–3.2 up to about 7.4–7.6 dependent on water in the formulation. The viscosity is dependent in part upon the water content, but is stable for at least a month and a half to two months. On the other hand, prior art products of sodium aluminum lactate have drifting or varying pH results from as low as 7 to as high as 10, with changes in pH of as much as 2.0 over a one to two day period.

The following examples of the present invention are illustrative:

EXAMPLE I—SOLID REACTANTS

| Formulation: | |
|---|---|
| Aluminum Lactate (Powder) | 35.0% |
| Sodium Hydroxide (Powder) | 10.0% |
| Water | 55.0% |

Charge water to vessel. While mixing, slowly add sodium hydroxide and mix until a uniform solution is produced. While mixing, slowly add aluminum lactate and mix until all dissolved.

The resulting product was subsequently spray dried with the following assay:

| Powder - Assay, Percentage | |
|---|---|
| Aluminum | 7.9 |
| Sodium | 14.1 |
| Lactic acid | 78.0 |

EXAMPLE II—AQUEOUS SODIUM HYDROXIDE

| Formulation: | |
|---|---|
| Aluminum lactate | 35.0% |
| Sodium hydroxide (50% aq.) | 16.0% |
| Water | 49.0% |

The same procedure as Example I ws used, except that aqueous sodium hydroxide instead of powder was added to the water.

The results of the spray dried product assay are:

| | |
|---|---|
| Aluminum | 7.9 |
| Sodium | 12.4 |
| Lactic acid | 79.7 |

What is claimed is:

1. A method of making sodium aluminum lactage, which comprises:
   first, mixing sodium hydroxide with water to form an aqueous sodium hydroxide solution; and, next, adding solid aluminum lactate thereto to produce sodium aluminum lactate.

2. The method of claim 1, wherein said mixing is performed within a temperature ranger of about 20° C. to about 80° C.

3. The method of claim 1 wherein the ratio of mixing aluminum lactate to sodium hydroxide, by weight, is about 5.0:1 to about 8.0:1.

4. The method of claim 1 wherein the ratio of mixing of aluminum lactate to sodium hydroxide, by weight, is about 5.0:1 to about 8.0:1.

5. The method of claim 3, wherein the ratio of water to sodium hydroxide, by weight, is about 0.8:1 to about 2.3:1.

6. A method of making sodium aluminum which comprises:
   combining a sodium hydroxide aqueous solution, water and aluminum lactate, and, producing sodium aluminum lactate within a temperature range of about 70° C. to about 80° C.

7. A method of making sodium aluminum lactate, which comprises:
   (a) mixing aluminum lactate with sodium hydroxide in an aqueous medium within a temperature range of about 25° C. and with a weight ratio of aluminum lactate to sodium hydroxide of about 5.0:1 to about 8.0:1 and a weight ratio of water to sodium hydroxide of about 0.8:1 to about 2.3:1.

8. The method of claim 7 which includes the step of first forming aluminum lactate by reacting lactic acid with aluminum.

9. The method of claim 7 which included the subsequent step of spray drying aqueous product obtained from said method to create a powder sodium aluminum lactate product.

10. The method of claim 7 wherein an aqueous solution of sodium hydroxide is formed and aluminum lactate is subsequently added thereto.

* * * * *